US012589173B2

(12) United States Patent
Eddy

(10) Patent No.: US 12,589,173 B2
(45) Date of Patent: Mar. 31, 2026

(54) STERILIZATION METHODS FOR STERILIZING A SURGICAL INSTRUMENT HAVING AN ANTIMICROBIAL COATING

(71) Applicant: Parasol Medical, LLC, Buffalo Grove, IL (US)

(72) Inventor: Patrick E. Eddy, Allendale, MI (US)

(73) Assignee: Parasol Medical, LLC, Buffalo Grove, IL (US)

( * ) Notice: Subject to any disclaimer, the term of this patent is extended or adjusted under 35 U.S.C. 154(b) by 757 days.

(21) Appl. No.: 17/218,445

(22) Filed: Mar. 31, 2021

(65) Prior Publication Data

US 2021/0299307 A1 Sep. 30, 2021

Related U.S. Application Data

(60) Provisional application No. 63/002,852, filed on Mar. 31, 2020.

(51) Int. Cl.
| | |
|---|---|
| *A61L 2/20* | (2006.01) |
| *A61L 2/08* | (2006.01) |
| *A61L 2/081* | (2026.01) |
| *A61L 2/10* | (2006.01) |
| *A61L 2/206* | (2026.01) |

(Continued)

(52) U.S. Cl.
CPC .............. *A61L 2/206* (2013.01); *A61L 2/081* (2013.01); *A61L 2/10* (2013.01); *A61L 2/208* (2013.01); *A61L 2101/02* (2020.08); *A61L 2202/24* (2013.01)

(58) Field of Classification Search
CPC ........ A61L 2/10; A61L 2202/24; A61L 2/081; A61L 2/206
See application file for complete search history.

(56) References Cited

U.S. PATENT DOCUMENTS

2001/0051669 A1* 12/2001 McGhee ................. A61L 2/087
523/112
2002/0141959 A1* 10/2002 Peterson .............. A61Q 17/005
514/63

(Continued)

FOREIGN PATENT DOCUMENTS

| CN | 101394747 B | * | 4/2013 | ............. A01N 25/02 |
|---|---|---|---|---|
| WO | WO-2012028196 A1 | * | 3/2012 | ............. A01N 31/02 |
| WO | WO-2016029010 A1 | * | 2/2016 | ............... A61L 2/00 |

OTHER PUBLICATIONS

English Translation of Foreign Publication No. CN 101394747 B entitled Water-Statbilised Antimicrobial Orgnosilane Products, Compositions, and Methods for using the same by R McMahon; Apr. 24, 2013 (Year: 2013).*

*Primary Examiner* — Kevin Joyner
(74) *Attorney, Agent, or Firm* — Price Heneveld LLP

(57) ABSTRACT

A sterilization method is provided for sterilizing a surgical instrument having an antimicrobial coating formed from applying a solution including a silane quaternary ammonium ion or salt thereof, the method comprising sterilizing the surgical instrument using a low temperature sterilization technique. The low temperature sterilization technique may include low temperature autoclave, exposure to ultraviolet light, exposure to gamma ray radiation, chemical sterilization, or any combination thereof. The chemical sterilization may include sterilization with ethylene oxide.

19 Claims, 1 Drawing Sheet

(51) Int. Cl.
_A61L 2/208_ (2026.01)
_A61L 101/02_ (2006.01)

(56) References Cited

U.S. PATENT DOCUMENTS

| | | | | |
|---|---|---|---|---|
| 2003/0063997 A1* | 4/2003 | Fryer | ................... | G01N 31/223 |
| | | | | 422/62 |
| 2007/0134302 A1* | 6/2007 | Koenig | ..................... | A61L 2/23 |
| | | | | 424/443 |
| 2007/0176117 A1* | 8/2007 | Redmond | ............. | A61M 39/16 |
| | | | | 250/455.11 |
| 2010/0291169 A1* | 11/2010 | Toreki | ............... | A61F 13/00995 |
| | | | | 521/38 |
| 2016/0303791 A1* | 10/2016 | Hannafin | ................... | A61L 2/07 |
| 2018/0242585 A1* | 8/2018 | Grossman | ............... | A61L 2/088 |

* cited by examiner

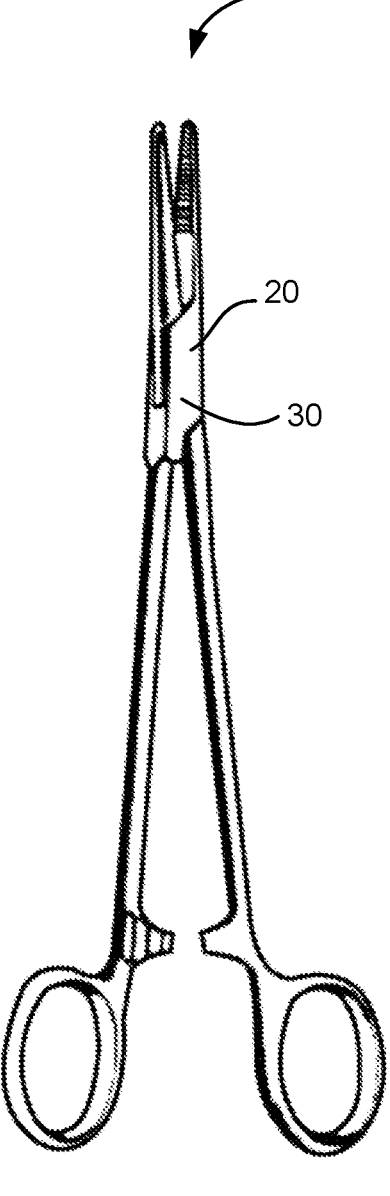

STERILIZATION METHODS FOR STERILIZING A SURGICAL INSTRUMENT HAVING AN ANTIMICROBIAL COATING

CROSS-REFERENCE TO RELATED APPLICATION

This application claims priority to and the benefit under 35 U.S.C. § 119 (e) of U.S. Provisional Patent Application No. 63/002,852, filed on Mar. 31, 2020, entitled "STERILIZATION METHODS FOR STERILIZING A SURGICAL INSTRUMENT HAVING AN ANTIMICROBIAL COATING," by Patrick E. Eddy, the entire disclosure of which is incorporated herein by reference.

BACKGROUND OF THE INVENTION

The present disclosure generally pertains to sterilization methods, and more particularly, sterilization methods suitable for sterilizing medical instruments having an antimicrobial coating. Surgical instruments are typically subjected to sterilization between uses. Such sterilization is often performed by placing the instrument in a high temperature autoclave. While sterilization is relatively easily performed in hospitals, military medical staff members may not always have means of sterilization available when working on the fringe of a battlefield. Thus, antimicrobial treatments have been considered for surgical instruments so that harmful microbes contacting the instrument may be killed on contact without need for sterilization.

While it is possible to treat medical instruments with such antimicrobial treatments, the instruments are not always used on the battlefield and thus may nevertheless be sterilized when sterilization means are available. However, the inventor discovered that high temperature autoclaves can damage the antimicrobial treatment and thereby reduce its effectiveness.

BRIEF SUMMARY OF THE INVENTION

According to a first aspect of the present disclosure, a sterilization method is provided for sterilizing a surgical instrument having an antimicrobial coating formed from applying a solution including a silane quaternary ammonium ion or salt thereof, the method comprising sterilizing the surgical instrument using a low temperature sterilization technique.

According to a second aspect of the present disclosure, a sterilization method is provided for sterilizing a surgical instrument having an antimicrobial coating formed from applying a solution including a silane quaternary ammonium ion or salt thereof, the method comprising sterilizing the surgical instrument using a low temperature sterilization technique wherein the silane quaternary ammonium ion or salt thereof is one or more of:

3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

According to a third aspect of the present disclosure, a sterilization method is provided for sterilizing a surgical instrument having an antimicrobial coating formed from applying a solution including a silane quaternary ammonium ion or salt thereof, the method comprising sterilizing the surgical instrument using a low temperature sterilization technique, wherein the silane quaternary ammonium ion or salt thereof is one or more of:

3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride; and wherein the low temperature sterilization technique includes sterilization with ethylene oxide.

These and other features, advantages, and objects of the present invention will be further understood and appreciated by those skilled in the art by reference to the following specification, claims, and appended drawings.

BRIEF DESCRIPTION OF THE DRAWING

In the drawings, FIG. 1 is a perspective view of a surgical instrument treated with an antimicrobial material.

DETAILED DESCRIPTION

For purposes of description herein, it is to be understood that the specific devices and processes illustrated in the attached drawings and described in the following specification are simply exemplary embodiments of the inventive concepts defined in the appended claims. Hence, physical characteristics relating to the embodiments disclosed herein are not to be considered as limiting, unless the claims expressly state otherwise.

Referring to FIG. 1, a surgical instrument in the form of forceps 10 is shown. Although forceps are shown and described below, forceps are just one example of surgical instruments that may be subjected to the sterilization method disclosed herein.

The surgical instrument 10 further includes an antimicrobial material 30 applied to, and at least partially covering the exterior surface 20 of the surgical instrument 10. The antimicrobial material 30 can additionally (or separately) be applied to anything attached to or part of the surgical instrument 10.

The antimicrobial material 30 may include a silane quaternary ammonium ion or salt thereof.

Preferred silane quaternary ammonium ions or salts thereof include:

3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

Applying the antimicrobial material 30 to the exterior surfaces 20 of the surgical instrument 10 imparts antimicrobial properties on the exterior surfaces 20, which prevents or lessens the ability of the exterior surfaces 20 to harbor harmful microbes, viruses, bacteria, and the like. Applying the antimicrobial material 30 to the exterior surfaces 20 serves to lessen the ability of the surgical instrument 10 to act as a vehicle that transmits the harmful microbes, viruses, bacteria, and the like to a patient.

Further described herein is a method of imparting antimicrobial properties onto any of the exterior surfaces 20 of any of the surgical instruments 10 described above. The method includes presenting a surgical instrument 10 with the exterior surface 20. The method further comprises applying to the exterior surface 20 of the instrument 10 a solution including the silane quaternary ammonium ion or salt thereof, as described above. In addition to the silane quaternary ammonium ion or salt thereof, the solution can further include a solvent. A preferred solvent is isopropyl alcohol.

The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution.

As for the isopropyl alcohol, the isopropyl alcohol can comprise between 30 percent and 90 percent by weight of the solution. More preferably, the isopropyl alcohol can comprise between 55 percent and 65 percent by weight of the solution. An example preferable solution comprises (by weight) 60.0 percent isopropyl alcohol, 2.02 percent 3-(trimethoxysilyl)propyldimethyloctadecyl ammonium chloride, and 34.19 percent deionized water.

Again, the solution can be applied to any exterior surface 20 of the surgical instrument 10 described above. The antimicrobial substance 30 can be a coating over the exposed surface 20. The isopropyl alcohol may be applied to the exposed surface 20 either simultaneously with the application of the antimicrobial substance 30 or before (or after) the application of the antimicrobial substance 30. Alternatively, the antimicrobial substance 30 alone may be applied to the exposed surface 20. In some embodiments, the antimicrobial substance 30 is bonded, either chemically or physically, to the exposed surface 20. In some embodiments, the surgical instrument 10 further comprises hydrogen peroxide applied to the exposed surface 20, either simultaneously with the application of the antimicrobial substance 30 or before (or after) the application of the antimicrobial substance 30 to the exposed surface 20. In embodiments, the surgical instrument 10 further comprises hypochlorous acid applied to the exposed surface 20, either simultaneously with the application of the antimicrobial substance 30 or before (or after) the application of the antimicrobial substance 30 to the exposed surface 20.

The surgical instrument 10 may subsequently be sterilized repeatedly between uses using a low temperature sterilization technique. As used herein, "low temperature" means at or below about 275° F. The low temperature sterilization technique may include low temperature autoclave (preferably performed in the range of 150-275° F.), exposure to ultraviolet light, exposure to gamma ray radiation, chemical sterilization, or any combination thereof. The chemical sterilization may include sterilization with ethylene oxide or glutaraldehyde (also known as gluteral). Ethylene oxide may be branded as Cidex® available from Advanced Sterilization Products (ASP) of Irvine, California.

It is to be understood that variations and modifications can be made on the aforementioned structure without departing from the concepts of the present invention, and further it is to be understood that such concepts are intended to be covered by the following claims unless these claims by their language expressly state otherwise.

The invention claimed is:

1. A between-use sterilization method for sterilizing a surgical instrument having an antimicrobial coating formed from applying a solution including a silane quaternary ammonium ion or salt thereof, the method comprising sterilizing the surgical instrument using a low temperature sterilization technique between uses.

2. The sterilization method of claim 1, wherein the low temperature sterilization technique includes low temperature autoclave.

3. The sterilization method of claim 1, wherein the low temperature sterilization technique includes exposure to ultraviolet light.

4. The sterilization method of claim 1, wherein the low temperature sterilization technique includes exposure to gamma ray radiation.

5. The sterilization method of claim 1, wherein the low temperature sterilization technique includes chemical sterilization.

6. The sterilization method of claim 5, wherein the chemical sterilization includes sterilization with ethylene oxide.

7. The sterilization method of claim 1, wherein, the silane quaternary ammonium ion or salt thereof is one or more of:
    3-(trimethoxysilyl)propyldimethyloctadecyl ammonium ion,
    3-(trimethoxysilyl)propyldimethyloctadecyl ammonium chloride,
    3-(trihydroxysilyl)propyldimethyloctadecyl ammonium ion, or
    3-(trihydroxysilyl)propyldimethyloctadecyl ammonium chloride.

8. The method of claim 1, wherein the solution further includes isopropyl alcohol.

9. The method of claim 8, wherein the silane quaternary ammonium ion or salt thereof is between 0.1 percent and 10 percent by weight of the solution.

10. The method of claim 9, wherein the isopropyl alcohol is between 30 percent and 90 percent by weight of the solution.

11. The method of claim 1, wherein the solution further includes hydrogen peroxide.

12. The method of claim 1, wherein the solution further includes hypochlorous acid.

13. A between-use sterilization method for sterilizing a surgical instrument having an antimicrobial coating formed from applying a solution including a silane quaternary ammonium ion or salt thereof, the method comprising sterilizing the surgical instrument using a low temperature sterilization technique between uses,
    wherein:
    the silane quaternary ammonium ion or salt thereof is one or more of:
        3-(trimethoxysilyl)propyldimethyloctadecyl ammonium ion,
        3-(trimethoxysilyl)propyldimethyloctadecyl ammonium chloride,
        3-(trihydroxysilyl)propyldimethyloctadecyl ammonium ion, or
        3-(trihydroxysilyl)propyldimethyloctadecyl ammonium chloride.

14. The sterilization method of claim 13, wherein the low temperature sterilization technique includes low temperature autoclave.

15. The sterilization method of claim 13, wherein the low temperature sterilization technique includes exposure to ultraviolet light.

16. The sterilization method of claim 13, wherein the low temperature sterilization technique includes exposure to gamma ray radiation.

17. The sterilization method of claim 13, wherein the low temperature sterilization technique includes chemical sterilization.

18. The sterilization method of claim 17, wherein the chemical sterilization includes sterilization with ethylene oxide.

19. A between-use sterilization method for sterilizing a surgical instrument having an antimicrobial coating formed from applying a solution including a silane quaternary ammonium ion or salt thereof, the method comprising sterilizing the surgical instrument using a low temperature sterilization technique between uses, wherein:

the silane quaternary ammonium ion or salt thereof is one or more of:

3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride; and wherein the low temperature sterilization technique includes sterilization with ethylene oxide.

\* \* \* \* \*